(12) United States Patent
Palmadesso et al.

(10) Patent No.: US 7,792,321 B2
(45) Date of Patent: Sep. 7, 2010

(54) HYPERSENSOR-BASED ANOMALY RESISTANT DETECTION AND IDENTIFICATION (HARDI) SYSTEM AND METHOD

(75) Inventors: Peter J. Palmadesso, Manassas, VA (US); Nielson W. Schulenburg, Herndon, VA (US); Daniel R. Stoffel, Redondo Beach, CA (US)

(73) Assignee: The Aerospace Corporation, El Segundo, CA (US)

( * ) Notice: Subject to any disclaimer, the term of this patent is extended or adjusted under 35 U.S.C. 154(b) by 829 days.

(21) Appl. No.: 10/901,542

(22) Filed: Jul. 28, 2004

(65) Prior Publication Data

US 2006/0023948 A1 Feb. 2, 2006

(51) Int. Cl.
*G06K 9/00* (2006.01)
(52) U.S. Cl. ...................................... 382/100
(58) Field of Classification Search ................. 382/103, 382/191; 702/3; 73/23.34
See application file for complete search history.

(56) References Cited

U.S. PATENT DOCUMENTS

| | | | |
|---|---|---|---|
| 5,124,915 A * | 6/1992 | Krenzel | 702/5 |
| 5,479,255 A * | 12/1995 | Denny et al. | 356/319 |
| 6,038,344 A * | 3/2000 | Palmadesso et al. | 382/191 |
| 6,075,891 A * | 6/2000 | Burman | 382/191 |
| 6,167,156 A * | 12/2000 | Antoniades et al. | 382/232 |
| 6,282,301 B1 * | 8/2001 | Haskett | 382/103 |
| 6,347,762 B1 * | 2/2002 | Sims et al. | 244/3.17 |
| 6,353,673 B1 * | 3/2002 | Shnitser et al. | 382/103 |
| 6,546,146 B1 * | 4/2003 | Hollinger et al. | 382/253 |
| 6,958,466 B1 * | 10/2005 | Stein | 250/221 |
| 7,194,111 B1 * | 3/2007 | Schaum et al. | 382/103 |
| 2004/0210391 A1 * | 10/2004 | Kolodner et al. | 702/3 |
| 2005/0160789 A1 * | 7/2005 | Freyer et al. | 73/23.34 |

OTHER PUBLICATIONS

Hyperspectral Image classification—approach, Joseph et al, IEEE, 0196-2892, 1994, pp. 779-785.*
Multisensor fusion—Classification., Hsu et al., Lincoln laboratory Journal., vol. 14 No. 1, 2003, pp. 145-159.*
Peter J. Palmadesso, Nielson W. Schulenburg, and Daniel R. Stoffel, "Integration of Real-Time Exploitation Subsystems with Hyperspectral IR Sensors," Military Sensing Symposium on Passive Sensors, Charleston, South Carolina, Apr. 2002.

* cited by examiner

*Primary Examiner*—Samir A. Ahmed
*Assistant Examiner*—Jayesh Patel
(74) *Attorney, Agent, or Firm*—Henricks, Slavin & Holmes LLP (57) ABSTRACT

A method for anomaly resistant detection and identification of an object signature in hypersensor data includes processing hypersensor data using a multi-dimensional matched filter to distinguish spectra that produce anomaly-generated false alarms from target spectrum, and suppressing the spectra that produce anomaly-generated false alarms.

12 Claims, 7 Drawing Sheets

HYPERSENSOR-BASED ANOMALY RESISTANT DETECTION AND IDENTIFICATION (HARDI) SYSTEM AND METHOD

TECHNICAL FIELD

The invention relates generally to processing hypersensor data and, in particular, to anomaly suppression technology.

BACKGROUND ART

Figure 1:
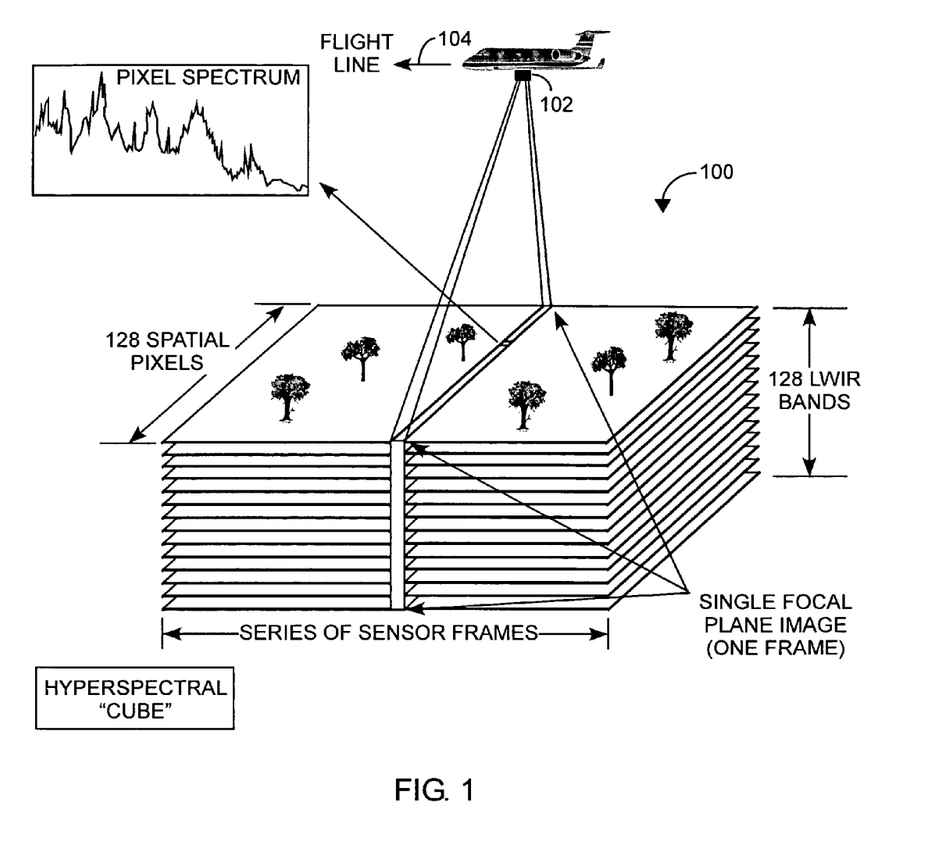
FIG. 1 illustrates an example of hyperspectral sensing.

A hyperspectral image is a three dimensional array of numbers $\{x_i, y_j, \lambda_k\}$, usually called a "cube", consisting of the intensities of light observed at each of a discrete set of wavelengths, and at every spatial pixel in a scene. A cube can be visualized as a stack of single band images of the spatial scene, with each layer representing a different wavelength band. FIG. 1 illustrates an example of a hyperspectral cube 100, which can be collected using a line scanner 102 such as the Spatially Enhanced Broadband Array Spectrograph System (SEBASS) sensor from The Aerospace Corporation of El Segundo, Calif. In this example, movement of the aircraft (or other object equipped with the line scanner 102) effects a ground path scan along a direction indicated by flight line arrow 104. By way of example, the line scanner 102 includes an array of Long Wave Infra-Red (LWIR) sensors that provide 128 LWIR bands (e.g., 7.8 to 13.5 μm, Δλ-0.04 μm) perpendicular to 128 spatial pixels, thus providing a series of sensor frames along the ground path scan direction.

Hyperspectral imaging (HSI) offers an extremely powerful tool for detecting solid targets or gaseous constituents in a complex background or mixture. The power of a hyperspectral system comes from the large number of individual wavelength bands in the spectrum of light collected at each "pixel" (spatial location) in a scene. By facilitating direct observation of spectral features at high resolution, over a broad range of wavelengths, hyperspectral imaging makes it possible to detect and identify many different materials, gases, etc., with a single system. In general, the spectral trace of a spatial pixel in a hyperspectral data cube will be influenced by several factors. These include emission from the target and atmosphere, absorption of light by the atmosphere or intervening gases, various atmospheric scattering effects, and, in the ultraviolet (UV) and visible through mid-wave infrared (MWIR) regimes, the characteristics of the light sources illuminating the scene. The light collected from a pixel may be dominated by a single object or substance, or by multiple objects, as in the case where the spatial resolution is insufficient to fully separate objects, or when light emitted by objects on the ground passes through a gas plume. Thus a given observed spectrum can be a complex mixture of characteristics of several different constituents. "Analysis" or "demixing" of hyperspectral data generally means detecting the presence and perhaps estimating the concentration of one or more specific objects or substances, by recognizing signatures of these substances in the spectral data. To this end, it would be useful to be able to suppress the influences of other entities (clutter) that may be mixed with the signature of interest in the spectrum collected at a given spatial location.

The most common approach to detection and quantification of pre-specified target signatures in mixed spectra involves use of a matched filter. A matched filter can be thought of as a mathematical operation performed on a data set that maximizes the influence of the desired signature in the output stream, while minimizing the influence of background clutter and noise. In the hyperspectral context, a matched filter is typically a high dimensional vector (denoted by F) that is approximately orthogonal to all the vectors that represent background and clutter signatures in the scene of interest, while having a significant projection on the particular target signature to which it is matched. Typically, the filter is scaled so that the dot product F·T=1, where T is a unit vector parallel to the target spectrum. Thus the filter output (i.e., the dot product of the filter with an observed spectral vector) can be used to infer the magnitude of the contribution of the target signature in the observed spectrum. If multiple targets are specified, each filter vector should also be orthogonal to all the other target signatures. Matched filters are derived via an optimization process. There are several approaches to deriving matched filters, depending on the details of the way the problem is posed, and what kind of a priori knowledge of the scene is available. The equations below illustrate a simple example of the optimization process, appropriate when there is no advance knowledge of the background, when there is a single target signature T, and when it is possible to select "training" spectra that contain all of the important background signatures but no target-bearing signatures:

Find F that minimizes the objective function C $$C = \sum_i (F \cdot d_{i\,training\,set})^2 + \lambda[F \cdot T - 1] \quad (1)$$

$$\Rightarrow F \propto \underline{\underline{M}}^{-}T$$

Where $\lambda$ is a Lagrange multiplier that adjoins the constraint F·T=1, $\{d_{i\,training\,set}\}$ is the "training set", and $\underline{\underline{M}}$ is the covariance matrix for the training set. The optimization described by equation (1) produces a filter vector F that is as nearly orthogonal to all the vectors $\{d_j\}$ in the training set as possible, subject to the constraint condition, which enforces the normalization condition mentioned above. In this example, optimization is a two-step process. First, a tractable mathematical idealization of the problem to be solved is constructed (step 1); then a good solution to the equations that embody the idealization is found (step 2). The phrase "Optimal Solution" usually means that step 2 has been done perfectly, but the quality of such a solution is limited by the error made in step 1. Better idealizations lead to better "optimal" solutions. The standard matched filter is optimal in the sense of step 2, but the mathematical idealization on which it is based has weaknesses. In fact, the use of the quadratic objective function C that defines the standard matched filter idealization (equation 1 and its more sophisticated analogues in conventional matched filter theory) is motivated primarily by considerations of mathematical convenience, i.e., by the fact that quadratic objective functions lead directly to linear systems of equations that are easy to solve, rather than a belief that this is the best possible representation of the problem.

As in any filter process, matched filters computed via equation (1) or similar equations are subject to false alarms and limitations on their ability to detect very weak targets (sensitivity). High false alarm rates can pose a serious threat to a sensor system: they reduce the user's confidence in the products of the system, and may also threaten its economic viability. The costs of the resources expended in response to a detection (e.g., firing an expensive missile, sending out a ground crew, etc.) are increased, sometimes dramatically, by the presence of false alarms. For this reason, analysts are usually employed to study and attempt to verify candidate detections when critical decisions must be based on these, but this process is also costly (again the cost scales with the false alarm rate), error-prone, and in many cases there is insufficient time to do it well, because HSI systems typically generate data at very high rates. For example, airborne HSI systems currently in operation may accumulate data at rates of the order of a gigabyte per minute or more. For applications that involve scanning a single site of modest size at a known location, or a small set of such sites, man-in-the-loop analysis and rejection of multiple false alarms is not an unduly burdensome problem, when it can be done accurately. On the other hand, applications involving wide area searches, e.g., military reconnaissance operations, search and rescue operations, natural resource surveys, etc., may require continuous collection over periods of many hours per day, for many days. In these cases, the task of analyzing the collected data and returning results in a timely fashion becomes very substantial, especially if a human analyst must guide the process, and a high false alarm rate may result in an intolerable operational burden, and in significantly reduced system reliability.

SUMMARY OF THE INVENTION

Example embodiments of the present invention include methods and systems for anomaly resistant detection and identification of an object signature in hypersensor data.

In example embodiments, the anomaly resistant detection and identification techniques generally involve processing hypersensor data (e.g., provided by an electronic nose or a chemical hypersensor) using a multi-dimensional matched filter to distinguish spectra that produce anomaly-generated false alarms from target spectrum and suppressing the spectra that produce anomaly-generated false alarms.

In example embodiments, the multi-dimensional matched filter distinguishes spectra uncommon in the scene and not orthogonal to the target that produce anomaly-generated false alarms from target spectrum, and suppresses the spectra uncommon in the scene and not orthogonal to the target that produce anomaly-generated false alarms.

In example embodiments, the multi-dimensional matched filter includes a set of orthogonally matched filters for one or more targets, and the matched filters are trained on common background only.

The orthogonally matched filters provide a multi-dimensional filter matrix that includes rows which form a set of mutually orthogonal filter vectors. The term "mutually orthogonal matched filters" means matched filters that are orthogonalized with each other.

In an example embodiment, a system for anomaly resistant detection and identification of an object signature in hypersensor data includes: a hypersensor (such as a chemical hypersensor which senses multiple different attributes of a chemical gas or vapor at each of multiple different observation times sensed by the chemical hypersensor and generates hypersensor data); and a mask and filter module configured to receive and process the hypersensor data using a multi-dimensional matched filter, such as described above, to distinguish spectra uncommon in the scene and not orthogonal to the target that produce anomaly-generated false alarms from target spectrum and suppress the spectra uncommon in the scene and not orthogonal to the target that produce anomaly-generated false alarms.

In example embodiments, a mask and filter module iteratively evolves a training mask that classifies pixels into one of two classes: "common background" (class 1) or "target and anomaly pixels" (class 2). The "target pixels" are the suspected target-bearing pixels. The "anomaly pixels" are pixel spectra with anomalous or unusual signatures.

In example embodiments, the mask and filter module also iteratively evolves a matched filter computed from the common background only; and the training mask is iteratively updated using products of the matched filter only.

In an example embodiment, a system for anomaly resistant detection and identification of an object signature in hypersensor data includes a hypersensor (such as a chemical hypersensor which senses multiple different attributes of a chemical gas or vapor at each of multiple different observation times sensed by the chemical hypersensor and generates hypersensor data), a mask and filter module, and an anomaly suppression module. The mask and filter module is configured to receive and process the hypersensor data to iteratively evolve: a training mask that classifies pixels into one of a group of classes consisting of a first class of pixels that includes common background, and a second class of pixels that includes target and anomaly pixels, the target and anomaly pixels being suspected target-bearing pixels and pixel spectra with anomalous or unusual signatures, respectively; and a matched filter computed from the common background only; wherein the training mask is iteratively updated using products of the matched filter only. The anomaly suppression module is configured to receive and process information pertaining to the matched filter and the common background, target and anomaly pixels to: determine for one or more targets a set of mutually orthogonal matched filters; use the mutually orthogonal matched filters to produce a vector of filter products for different spectra of the common background, target and anomaly pixels; and compare elements of the vectors to determine whether pixel spectrum should be rejected as an anomaly.

DISCLOSURE OF INVENTION

Example embodiments of the present invention pertain to a system and method for rapid automated processing of data collected by a hypersensor in order to detect and identify members of a predefined set of "target" species embedded in complex unknown backgrounds. The system and method described herein offer higher sensitivity and a substantially lower likelihood of false alarms than is possible with standard methods.

For the purposes of this description, a "hypersensor" is defined as a sensor whose output takes the form of a high-dimensional vector, each element of which quantifies some attribute of the received signal. Principles of the HARDI system and method described herein have been successfully implemented in a real-time Long Wave Infra-Red (LWIR) Hyperspectral Imaging system, based on the SEBASS sensor. In the following description, reference is made to Long Wave Infra-Red (LWIR) hyperspectral imaging (HSI) systems as a particular example of a hypersensor application. It should be understood, however, that a hyperspectral imaging system is but one example of a hypersensor, and that the principles described herein are not limited to optical sensors or imaging systems.

Methods and systems of the present invention address the primary way in which standard high dimensional matched filter algorithms generate false alarms from natural or sensor-generated anomalies. Principles of the present invention can be used for implementation of an exploitation system capable of processing HSI (or other hypersensor) data in real time, with substantially reduced false alarm rates and some increased sensitivity. The false alarm generation mechanism and an approach to mitigating this problem according to the present invention are described below.

False Alarm Generation Mechanism

The false alarm generation mechanism of interest can be described in terms of a geometric interpretation of a high dimensional matched filter. For simplicity, a single target signature is considered, but the generalization to the multi-target case is straightforward. Recall from above the properties of a standard high dimensional matched filter:

$$F \cdot T = 1 \text{ and } F \cdot B_j \approx 0 \quad (2)$$

In the equations above, T is a unit vector in the direction of the target signature, and $B_j$ is any member of a set of vectors that together span the subspace that contains the background clutter signatures $\{d_i\}$, to within some error tolerance, $\epsilon$. For exact clutter rejection ($\epsilon \to 0$), the background clutter typically fills the full spectral space, and it becomes impossible to find a solution. Thus there is always some residual clutter that is not suppressed by the filter. Given a filter that satisfies the equation pair (2) and a data vector $d_i$ that is the sum of a noise contribution $N_i$, a clutter contribution $b_i$, and a target contribution $a_i T$ ($a_i = 0$ if no target is present) then $$F \cdot d_i = F \cdot (N_i + b_i + a_i T) = a_i + |F| \times (\text{small errors due to noise and residual clutter}) \quad (3)$$

Figure 2:
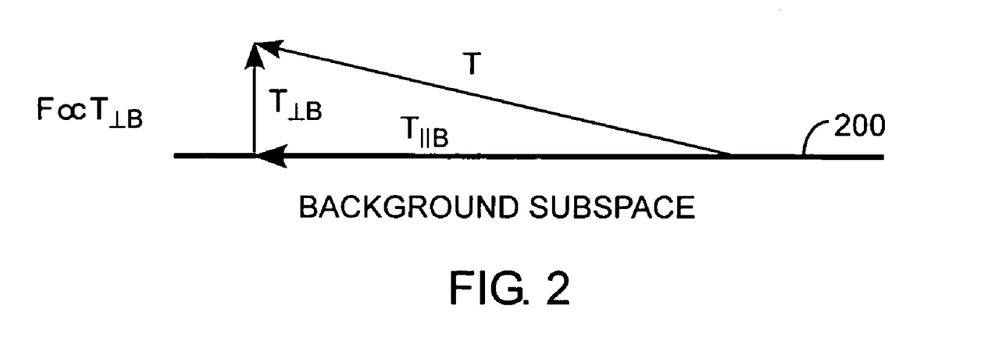
FIG. 2 represents an example hyperplane that contains (approximately) clutter spectral vectors.

Since the filter F must be orthogonal to the background clutter (approximately) but not orthogonal to the target vector, it follows that F must be parallel to $T_{\perp B}$, the portion of the target signature that is orthogonal to all the clutter spectra, as illustrated in FIG. 2.

In FIG. 2, the line 200 labeled "Background subspace" represents the hyperplane that contains (approximately) the clutter spectral vectors. The present invention exploits an understanding of the mechanism by which the conventional matched filter mathematics produce false alarms. According to the present invention, it has been observed that |F|, the magnitude of the filter vector, must grow as the clutter subspace expands to capture more of the target spectrum. Every time a new background signature that is not already orthogonal to the target signature is learned, $T_{\|B}$, the projection of the target spectrum in the space spanned by the background, grows (because more of the target vector has been captured by the clutter subspace), and $T_{\perp B}$ shrinks, making $T_{\perp B}$ (and F) more nearly orthogonal to T. Since T is a unit vector, the constraint condition $F \cdot T = 1$ yields $$|F| = \frac{1}{\cos(\sphericalangle F, T)} = \frac{1}{\cos(\sphericalangle T_{\perp B}, T)} \quad (4)$$

where $\cos(\sphericalangle T_{\perp B}, T)$ is the cosine of the angle between $T_{\perp B}$ and T. Thus |F| grows as new background signatures are learned. To illustrate how this generates false alarms, consider a simple case in which there are just two background spectra, a very common clutter species, and a very rare one, which will be referred to as an anomaly. The value of the objective function in equation (1) can be represented as follows, in this case:

$$C \approx N_{anomaly}(\overline{F \cdot d_{anomaly}})^2 + N_{common}|F|^2(\sigma_{noise}^2 \sigma_{clutter\ residue}^2) \quad (5)$$

The constraint term has a value of zero when the constraint is satisfied, and therefore makes no contribution. The common clutter species, which is assumed to have been "learned", makes a contribution that depends on the magnitudes of the noise, the residual clutter (if any), and the magnitude of the filter vector as shown in (5). The common clutter contribution to the final value of the objective function is the sum of the small error terms in equation (2), and is proportional to the square of the magnitude of the filter. Here $\sigma_{noise}^2$ and $\sigma_{clutter\ residue}^2$ are the variances of the noise and clutter residue components of the set of pixel spectra that form the cube. These are both small, but their contribution to C is multiplied by a very large number, $N_{common}$, which is the number of pixels that contain the common clutter signature. In contrast, the anomaly contribution comes from a very small number of pixels. There is a trade-off to be made: if the algorithm "learns" the anomaly spectrum, i.e., if the filter is made nearly orthogonal to the anomaly spectral vector as well as the common clutter vector, then the anomaly makes a small per-pixel contribution in a small number of pixels, but the common clutter contribution is increased, because learning the anomaly results in an increase in |F|, and this in turn results in a significant increase in the cumulative "cost" of the common clutter contribution. It also results in an increase in the size of the error made in every one of the common pixels, resulting from equation (3), and therefore decreased sensitivity. On the other hand, if the anomaly is simply ignored, a significant cost is paid in a few pixels, and some savings are realized in each of the common pixels. In many cases, the penalty paid in the common clutter term is greater than the cost of ignoring the anomaly, and the minimum value of the objective function is achieved by ignoring the anomaly. The resulting filter is not orthogonal to the anomaly, and so produces a false alarm, even when the anomaly spectrum is not at all similar to the target spectrum. In summary, sensor glitches and rare clutter species produce anomalies, and conventional matched filter mathematics turn some of those anomalies into false alarms. Moreover, the conventional approach actually produces false alarms as a direct consequence of the quadratic objective function idealization upon which the optimization is based.

Mitigation Strategy

As discussed above, an attempt to address the problem posed by anomaly-generated false alarms by forcing the algorithm to "learn" the anomaly signatures would result in a loss of sensitivity: the resulting increase in the magnitude of the filter would produce an increase in the magnitude of the noise and residual clutter errors (see equation 3), and a concomitant increase in the Minimum Detectable Quantity (MDQ) of target in the scene. According to the present invention, this problem is avoided by employing a two-step detection process as described below. In step one, a filter is produced from a training set that has been purged not only of suspected target-bearing pixels but also of as many of the pixel spectra with anomalous or unusual signatures as possible. This process yields a filter trained on common background only, which has high sensitivity to targets mixed with common background but also a high false alarm rate, because the algorithm is not allowed to learn the anomalies. In step two, most of the anomaly-generated false alarms are suppressed by application of a mathematical operation designed to distinguish between real targets and anomalies, in observed spectra mixed with background clutter signatures. The result is a filter operation with increased sensitivity and reduced false alarm rates.

The post-processing operation in step two exploits the observation of the present invention that the spectra that produce anomaly-generated false alarms are not, in general, very similar to the target spectrum: they are merely spectra that are uncommon in the scene and not orthogonal to the target. Hence, discrimination between real targets and anomaly-generated false alarms can be accomplished by devising a computable measure of similarity between the signature embedded in a pixel of interest and the target spectrum. The comparison is complicated by the fact that the observed pixel spectrum may also contain some unknown combination of common clutter signatures, which should be taken into account. For example, a comparison based on the angle between the observed spectrum and the target spectrum will not work well, in general, if the target presence is weak and background signatures are mixed in with the observed spectrum.

Figure 3:
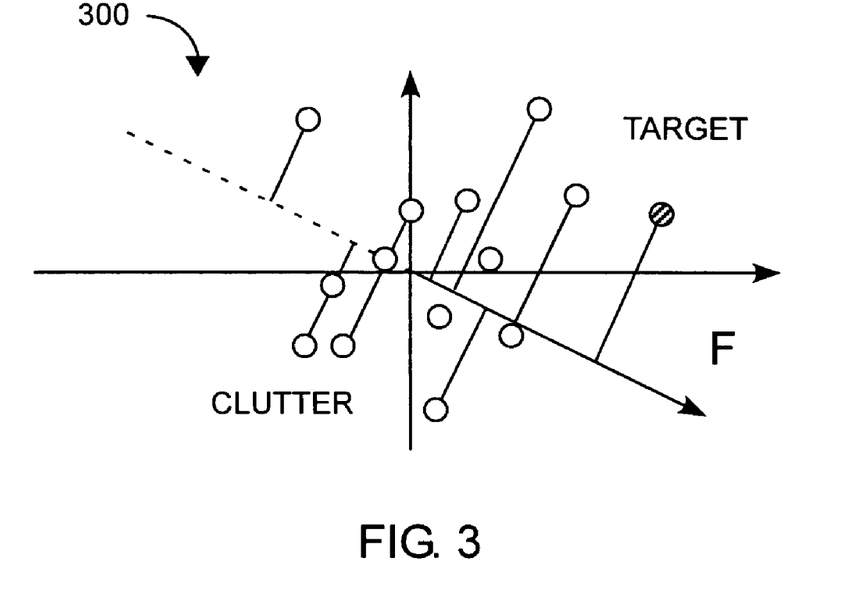
FIG. 3 illustrates an example high dimensional band space with spectral vectors.

In an example embodiment of the present invention, the discrimination operation combines a multi-dimensional matched filter operation with a statistical decision process. With respect to the operation of single-vector matched filters, FIG. 3 illustrates a high dimensional band space 300. The dots in FIG. 3 represent spectral vectors: they are points in the high dimensional band space 300. The filter vector defines a ray in band space such that the projections of the clutter spectra on the filter ray are well separated from the projection of the target spectrum. A standard HSI matched filter may be viewed in this way, and represents the "optimal" projection direction, though as has been discussed, it is optimal only within the context of a particular idealization of the problem, and that idealization is somewhat flawed. In a two-dimensional space such as in FIG. 3 there may be only one projection direction that does a reasonable job of separating the target from the clutter. In the much higher dimensional spaces associated with hypersensor data, there are likely to be several orthogonal projection directions that do a good job of separating the target from the clutter. According to embodiments of the present invention, by minimizing an appropriate series of objective functions, an optimal Multi-Dimensional Filter (MDF) matrix can be constructed, the rows of which form a set of mutually orthogonal filter vectors $\{F^{(n)}\}$, each of which satisfies, in addition to the orthogonality constraints, a normalization condition of the form $$F^{(n)} \cdot T = 1 \qquad (6)$$

The objective function used to determine the $n^{th}$ order filter, $F^{(n)}$, can be equation (1), or any of several common variants thereof, plus an additional set of constraints that insure that $F^{(n)}$ is orthogonal to all of the lower order filters. The number of rows in the MDF matrix depends on the dimensionality of the dataset, the statistics of the clutter, and the angular relationships between the target spectrum and the clutter vectors, and can be computed by consideration of these factors. In general, $F^{(0)}$, the ordinary matched filter, is the best filter, $F^{(1)}$ is the second best, and so on. The ratio of target to clutter and noise decreases as n increases, until the addition of another filter would have no significant value. By way of example, the clutter variance along each new filter direction is monitored during the filter generation process, and the operation terminates when the signal-to-clutter ratio falls below a predetermined threshold, or when the number of filters in the MDF set reaches a preset maximum value.

Matrix multiplication of the MDF matrix with an observed spectral vector yields a filter product in the form of a vector with $D_{MDF}$ elements, where $D_{MDF}$ is the number of MDF vectors for the target currently being considered. In a multi-target case, which can be treated using a generalization, each target has its own MDF matrix, and $D_{MDF}$ may be different for different targets. The normalization constraint in equation (6) means that, to within an error due to noise and residual clutter, the value of every element of the MDF product vector associated with a real target in common background will be the same (the actual value depends on how much target is present). In contrast, an anomaly-generated false alarm will, in general, produce a spread of values within the set of MDF product elements. Thus, according to an example embodiment of the present invention, real targets and anomaly-generated false alarms are distinguished by analyzing the spread (differences) in the MDF product values: if the variability in the elements is consistent with that expected from noise and residual common clutter, the result is accepted as real; if not, it is rejected. In the multi-target case, it is most convenient to implement the statistical test by first subtracting from each filter product the projection of the target mixture predicted by the zero-order (best) filters for the various targets. Then the MDF product elements for a pixel containing a valid target should be consistent with residual noise and clutter, and the statistical test is performed accordingly. Noise statistics are determined during the sensor calibration process and are assumed known, and residual clutter statistics can be inferred from the training set. The actual decision process can take any of several forms, using parametric or non-parametric statistical methods.

In an example embodiment, a method for anomaly resistant detection and identification of an object signature in hypersensor data includes receiving hypersensor data, processing the hypersensor data using a filter trained on common background only to generate a filter output, and suppressing anomaly-generated false alarms in the filter output by distinguishing between real targets and anomalies, in observed spectra mixed with background clutter signatures.

Figure 4:
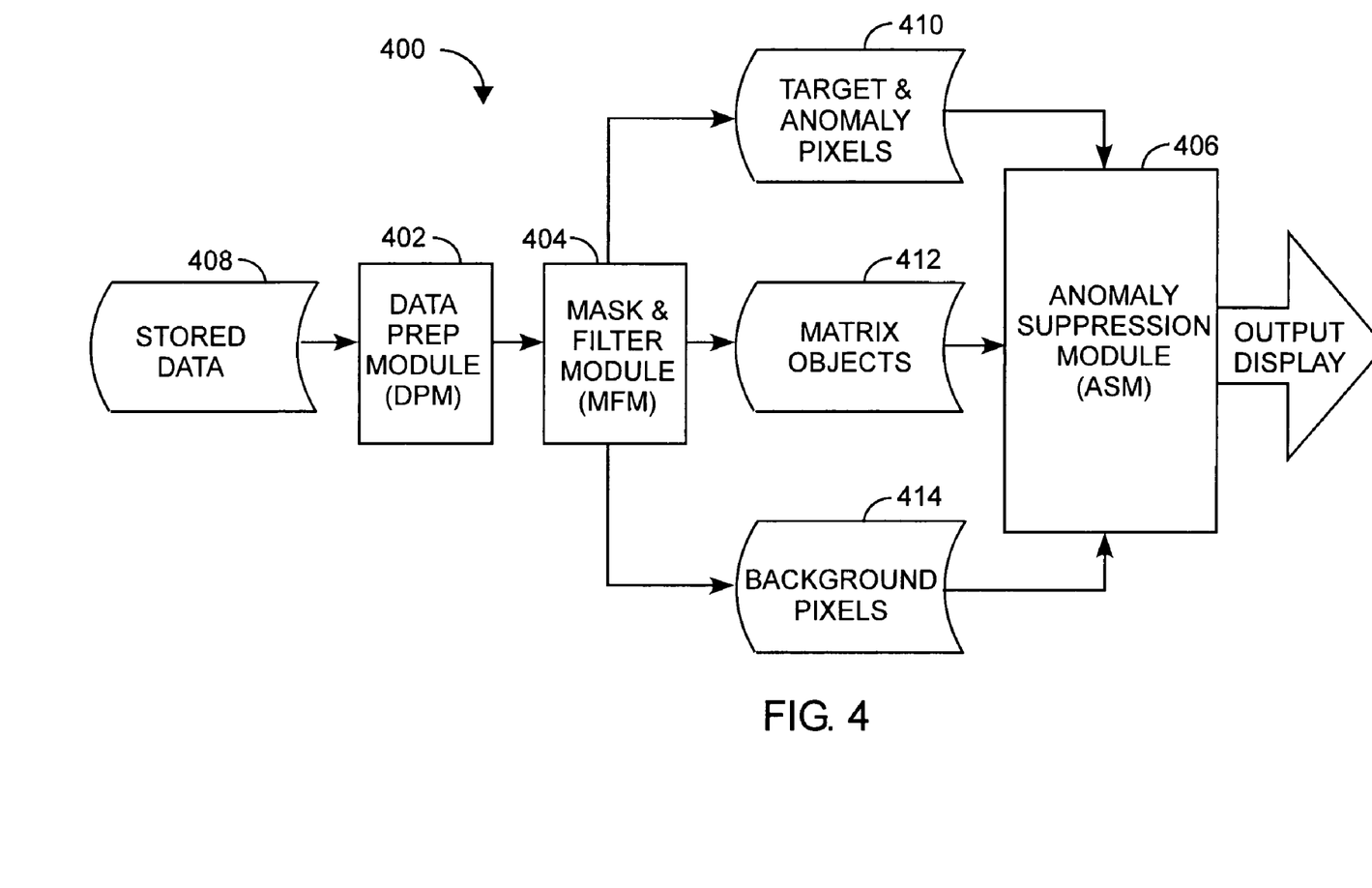
FIG. 4 illustrates an example embodiment of a detection and identification system.

Referring to FIG. 4, an example embodiment of a detection and identification system 400 includes a Data Preparation Module (DPM) 402, a Mask & Filter Module (MFM) 404 and an Anomaly Suppression Module (ASM) 406, configured as shown. In this example embodiment, the Mask & Filter Module (MFM) 404 and the Anomaly Suppression Module (ASM) 406 are the operational elements of the system 400 that implement the two-step process described above. In this example embodiment, the Data Preparation Module (DPM) 402 is configured to fetch and prepare stored data 408. The Data Preparation Module (DPM) 402 can be configured to implement calibration procedures and other operations to set up the data. For example, the data can be projected into a reduced dimensional subspace, such as a space spanned by a chosen subset of the Principal Component (PC) vectors, in order to reduce the computational burden and further condition the data. In this example embodiment, the Anomaly Suppression Module (ASM) 406 receives and processes (data for) Target and Anomaly Pixels 410, Matrix objects 412, and Background Pixels 414 to display the results.

Figure 5:
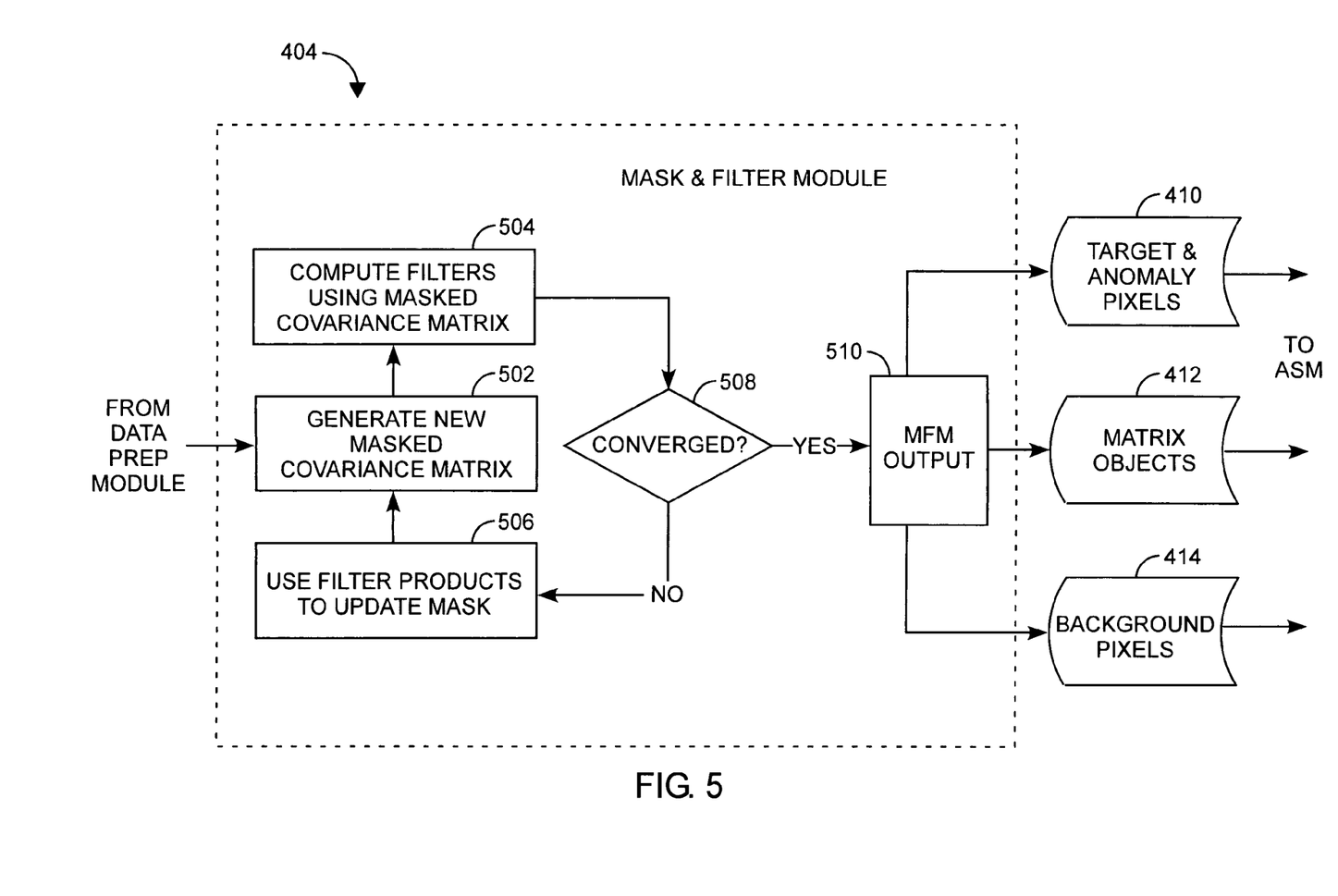
FIG. 5 illustrates the operation of the Mask & Filter Module of the detection and identification system of FIG. 4.

FIG. 5 illustrates the operation of the Mask & Filter Module (MFM) 404. In this example embodiment, the Mask & Filter Module (MFM) 404 employs an iterative procedure that simultaneously evolves a "training mask" and a simple matched filter computed using the training data. The training mask is an array the same size and shape as the scene segment that generates the hyperspectral cube, with a zero or a one at each spatial pixel location, indicating that the pixel is (one) or is not (zero) part of the training set. Intermediate values representing partial membership in the training set (in a fuzzy logic sense) can also be used. By way of example, initially all elements of the training mask are set to one. A simple matched filter is then computed and applied to the hyperspectral cube. Pixels that return values that are above a threshold value, for example, some multiple of the median of the set of absolute values of the filter products, are cast out of the training set (they are target bearing pixels or anomalies) and the corresponding element of the training mask is set to zero. A new matched filter is computed from the new training set and applied to the entire cube (not just the training pixels), and a new mask is computed. With reference to FIG. 5, a new masked covariance matrix is generated at step 502, and filters are computed using the masked covariance matrix at step 504. The process is repeated (using the filter products to update the mask at step 506) until it converges (at step 508), yielding a matched filter computed from common background, and a training mask that classifies the pixels into common background (class 1) or target and anomaly pixels (class 2). The pixel spectra, along with the matched filter and some other mathematical objects, such as the common background covariance matrix computed during the filter evolution process (in FIG. 5, the Target and Anomaly Pixels 410, Matrix objects 412, and Background Pixels 414), are passed (at step 510) along to the Anomaly Suppression Module (ASM) 406.

Figure 6:
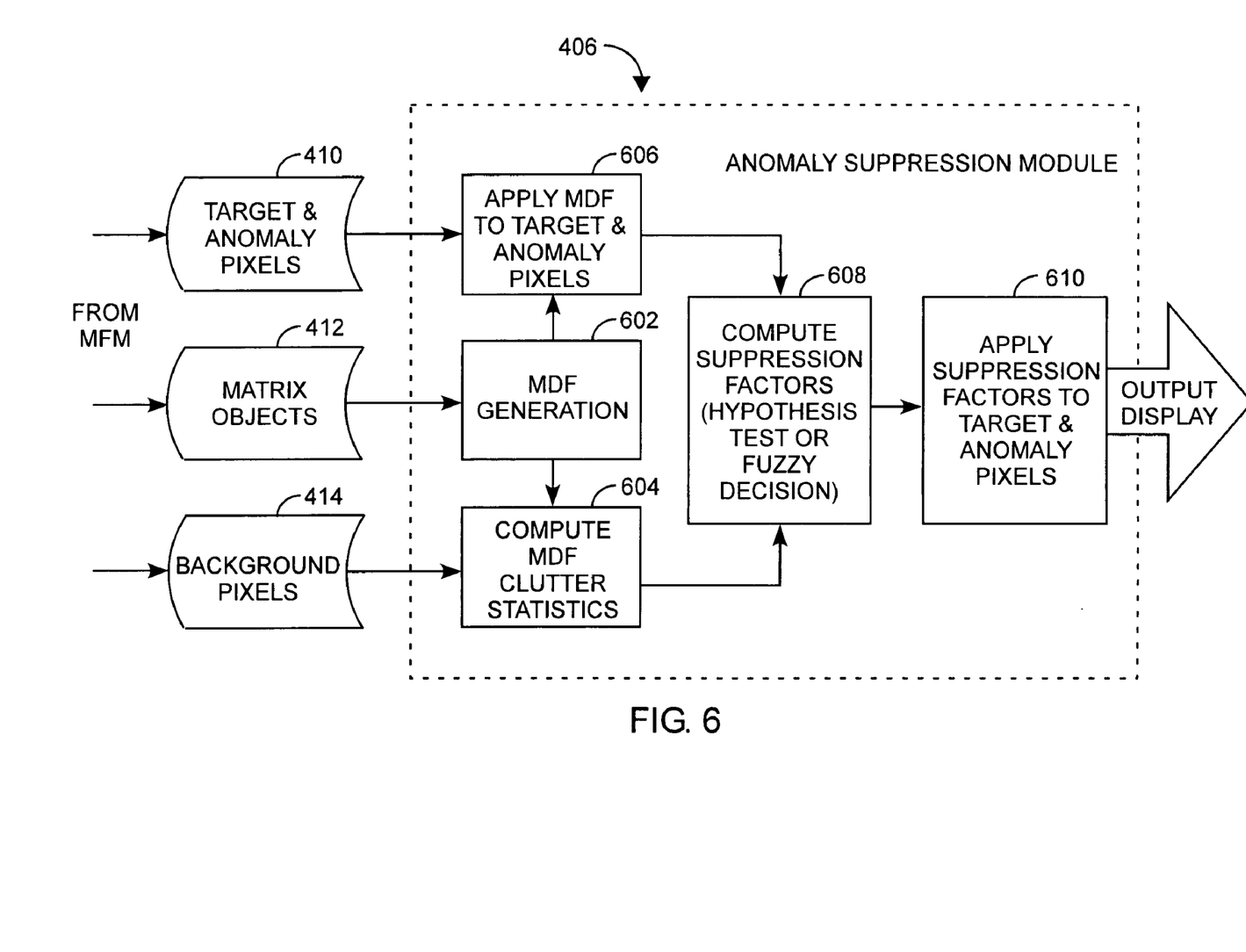
FIG. 6 illustrates the operation of the Anomaly Suppression Module of the detection and identification system of FIG. 4.

FIG. 6 illustrates the operation of the Anomaly Suppression Module (ASM) 406. In this example embodiment, the information provided by the MFM is used to find, for each target, a set of mutually orthogonal matched filters that together form a multi-dimensional matched filter (MDF). By way of example, given the training set evolved in the MFM, a series of optimization problems can be solved by generalizing the standard matched filter mathematics (equation 1 or any of several common variations) to include an additional set of constraints. At each stage, the condition that the new optimal filter must be orthogonal to all the lower order filters for the target being considered is added to the cost function used in the first stage (equation 1 or similar). Thus, the zero order filter is the standard matched for the training set, the first order filter is the optimal matched filter subject to the additional constraint that it is orthogonal to the zero order filter, and the $n^{th}$ order filter minimizes the cost function subject to the additional constraints that ensure it is orthogonal to filters of order zero through (n−1). Every member of the MDF set also satisfies the requirement that its dot product with its corresponding target has the value unity. With reference to FIG. 6, the MDF is generated at step 602. At each stage, the variance of the common clutter along the new filter direction is computed (at step 604), stopping when the signal to clutter ratio, computed for some reference signal strength, falls below a preset threshold. The MDF set then operates (at step 606) on the class 2 (anomalies and target bearing) pixel spectra, to produce a vector of filter products for each spectrum. The MDF product vector for each class 2 pixel spectrum is compared (at step 608) with the result produced by applying the MDF set to the target mixture spectrum predicted by the zero order filters (these are the most sensitive) for each target. A statistical test is then performed to determine if the differences in the elements of these two vectors are consistent with the hypothesis that they are the result of noise and common clutter. If not, the pixel spectrum is rejected (at step 610) as an anomaly. It should be appreciated that variations in the MDF decision process implementation can be employed, within the HARDI framework or otherwise.

In an example embodiment, a system for anomaly resistant detection and identification of an object signature in hypersensor data includes a mask and filter module and an anomaly suppression module. The mask and filter module is configured to receive and process hypersensor data to iteratively evolve a training mask that classifies pixels into common background or target and anomaly pixels, and a matched filter computed from the common background. The anomaly suppression module is configured to receive and process information pertaining to the matched filter and the common background, target and anomaly pixels to determine for one or more targets a set of mutually orthogonal matched filters, use the mutually orthogonal matched filters to produce a vector of filter products for different spectra of the common background, target and anomaly pixels, and compare elements of the vectors to determine whether pixel spectrum should be rejected as an anomaly.

In an example embodiment, a method for anomaly resistant detection and identification of an object signature in hypersensor data includes processing hypersensor data using a multi-dimensional matched filter to distinguish spectra that produce anomaly-generated false alarms from target spectrum, and suppressing the spectra that produce anomaly-generated false alarms.

Figure 7:
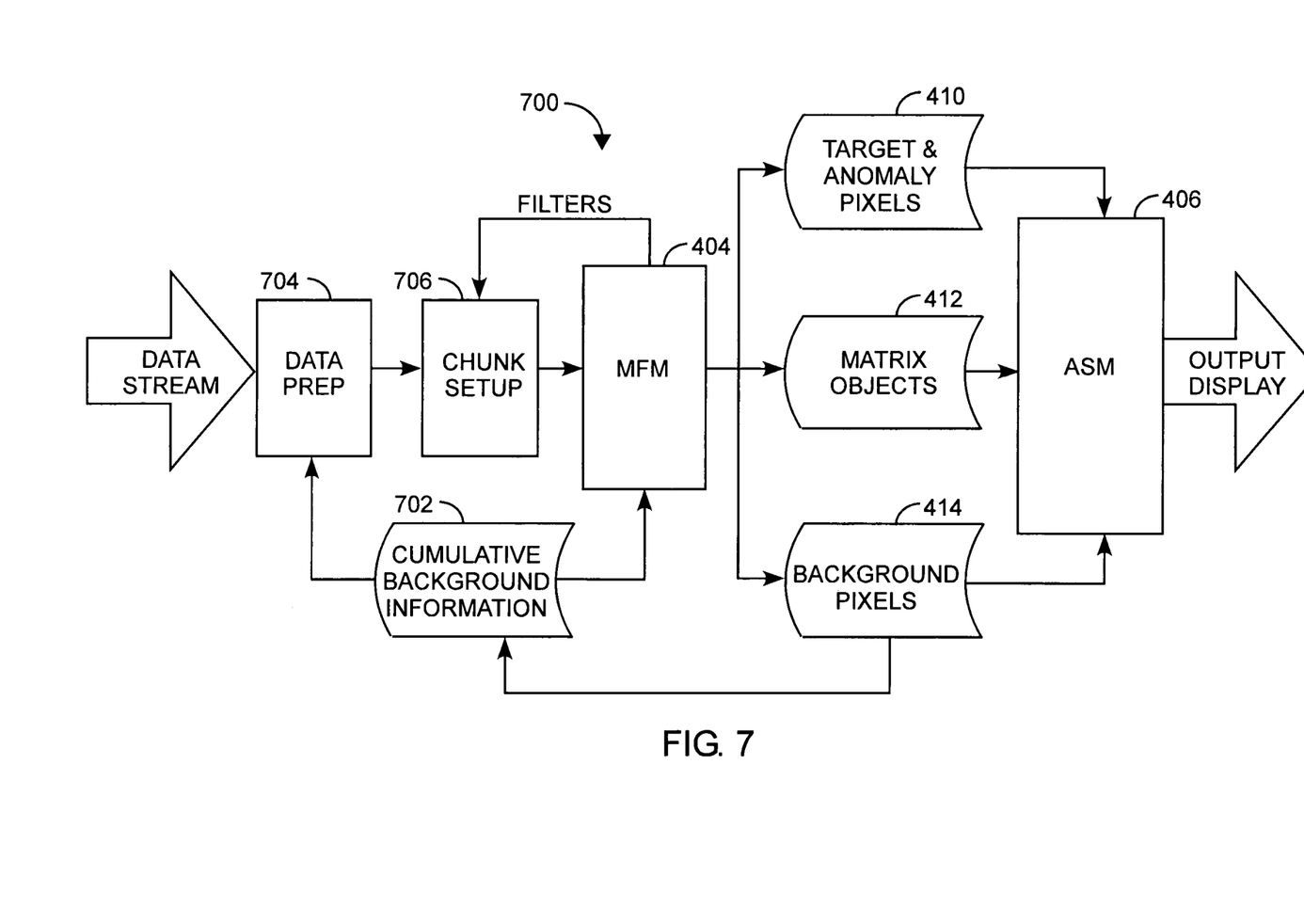
FIG. 7 illustrates an example embodiment of a detection and identification system including an additional process thread, as compared to the detection and identification system of FIG. 4.

FIG. 7 illustrates an example embodiment of a detection and identification system 700 including a logic structure for an additional process thread, as compared to the system of FIG. 4. In this example embodiment, a real time HSI implementation of HARDI is implemented. The additional process thread partitions the data stream into small chunks for rapid processing, and provides a mechanism for storing and applying information about background signatures learned in previous chunks. With reference to FIG. 7, cumulative background information 702 is provided to a data preparation module 704, and filters generated by the MFM 404 are provided to a chunk setup module 706 configured between the data preparation module 704 and the MFM 404 as shown. An example description of methods for breaking the data stream into chunks and combining information in the current chunk with background characterization information remembered from previous chunks is provided in Peter J. Palmadesso, Nielson W. Schulenburg, and Daniel R. Stoffel, "Integration of Real-Time Exploitation Subsystems with Hyperspectral IR Sensors," Military Sensing Symposium on Passive Sensors, Charleston, S.C., April 2002, which is incorporated herein by reference.

The embodiments described above, in which the MFM and AFM operations are applied in two separate steps, are well suited for fast automated stand-alone and real-time systems, when computing power is limited by weight restrictions or other considerations. Alternative embodiments in which the MFM and AFM operations are more tightly coupled are also possible. For example, the statistical test on the MDF product elements can be used within the MFM iteration, e.g., step 506 in FIG. 5, to help identify pixels that contain only common background, and thereby aid in the selection of training mask pixels. Embodiments of this type generally require greater computational resources, and may produce better results in some applications.

Signature-based hyperspectral systems operating in other spectral ranges (ultra-violet, visible, near-IR, mid-wave, etc.) can also be implemented to employ the HARDI method for the purpose of providing reduced false alarm rates, improved sensitivity, and fast response. In addition to military applications, such systems are potentially applicable to problems in precision agriculture, mining, environmental assessment, pollution detection, search and rescue, medical imaging, and many other problem areas.

Figure 8:
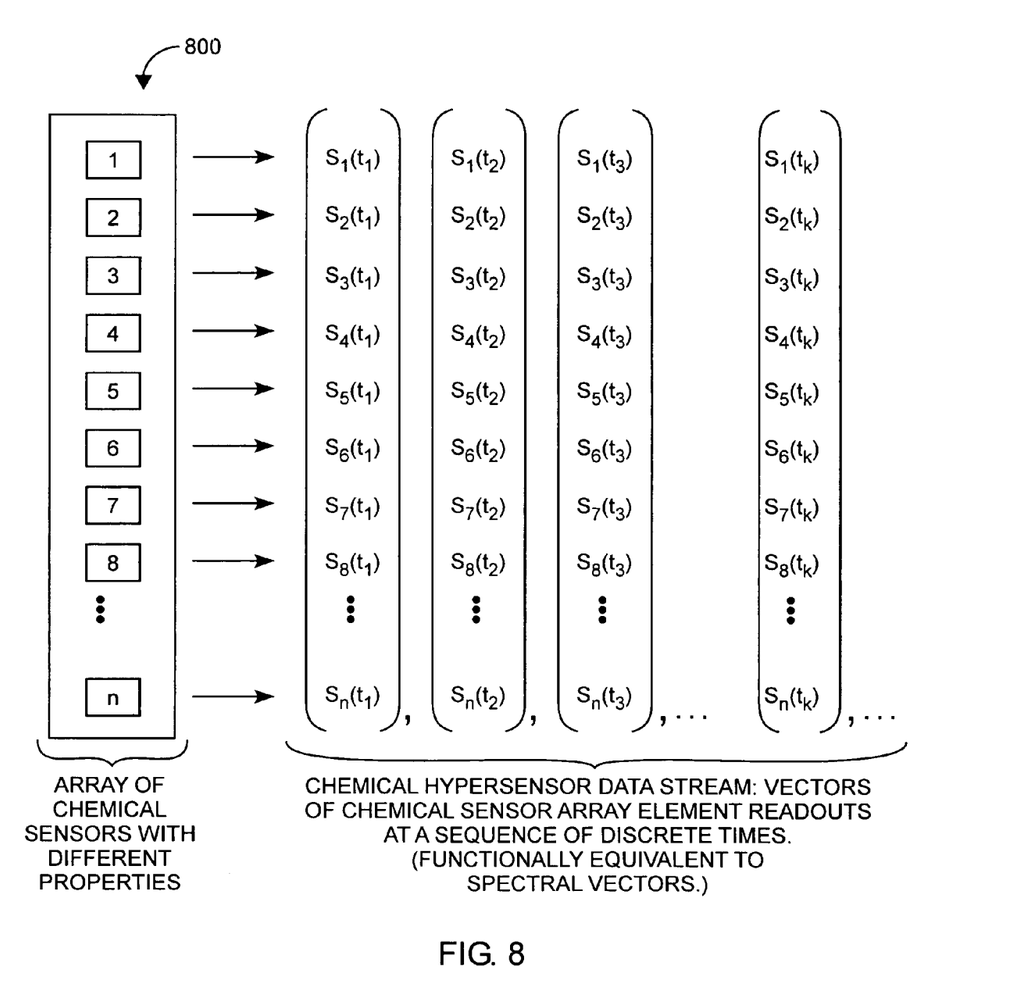
FIG. 8 is a schematic of an example chemical hypersensor.

As previously noted, the potential value of HARDI is not limited to optical hypersensors or imaging systems: once the data stream is cast in the form of a stream of high-dimensional vectors, the HARDI process is insensitive to the kind of sensor that generated the stream. For example, in recent years electro-chemical hypersensors, often called "electronic noses", have been developed in order to emulate the ability of human and animal olfactory systems to detect and identify airborne chemicals at extremely low concentrations. As illustrated in FIG. 8, an example artificial nose is an array 800 of electro-chemical sensor elements whose electrical characteristics change slightly in the presence of gases or weak chemical traces. A single element gives little useful information, but a large array of non-identical elements, such as different kinds of membranes, yields a vector response (a spectrum) that exhibits different patterns for different chemicals. Electronic noses have been used to detect diseases by sensing weak chemical traces in human breath, and have many other applications. In electronic nose application environments where signals of interest must be reliably detected in changeable mixtures of other constituents, and where anomaly generated false alarms would be detrimental to performance, the HARDI technology is likely to prove valuable.

Hyper-acoustic imaging systems that return a full acoustic frequency response spectrum at each spatial location have been developed and shown to be capable of detecting imperfections in solid materials without the use of high powered X-ray machines, which are not easily portable. Other hyper-acoustic applications are likely to be found, and systems of this type may provide additional opportunities to apply HARDI.

The class of hypersensor exploitation problems that HARDI addresses, involving the timely and reliable detection of pre-specified constituents in variable unknown mixtures of other constituents, is not limited to the hypersensor applications described herein.

Although the present invention has been described in terms of the example embodiments above, numerous modifications and/or additions to the above-described embodiments would be readily apparent to one skilled in the art. It is intended that the scope of the present invention extends to all such modifications and/or additions.

We claim:

1. A system for anomaly resistant detection and identification of an object signature in hypersensor data, comprising:
    a chemical hypersensor which senses multiple different attributes of a chemical gas or vapor at each of multiple different observation times sensed by the chemical hypersensor and generates hypersensor data; and
    a mask and filter module configured to receive and process the hypersensor data to iteratively evolve
        a training mask that classifies pixels into one of a group of classes consisting of
            a first class of pixels that includes common background, and
            a second class of pixels that includes target and anomaly pixels, the target and anomaly pixels being suspected target-bearing pixels and pixel spectra with anomalous or unusual signatures, respectively, and
        a matched filter computed from the common background only,
        wherein the training mask is iteratively updated using products of the matched filter only; and
    an anomaly suppression module configured to receive and process information pertaining to the matched filter and the common background, target and anomaly pixels to
        determine for one or more targets a set of mutually orthogonal matched filters,
        use the mutually orthogonal matched filters to produce a vector of filter products for different spectra of the common background, target and anomaly pixels, and
        compare elements of the vectors to determine whether pixel spectrum should be rejected as an anomaly.

2. The system for anomaly resistant detection and identification of an object signature in hypersensor data of claim 1, wherein the hypersensor data represents a hyperspectral cube.

3. The system for anomaly resistant detection and identification of an object signature in hypersensor data of claim 1, wherein the training mask is an array that is the same size and shape as a scene segment from which the hypersensor data was generated.

4. The system for anomaly resistant detection and identification of an object signature in hypersensor data of claim 1, wherein the anomaly suppression module is configured to perform a statistical test to determine whether pixel spectrum should be rejected as an anomaly.

5. The system for anomaly resistant detection and identification of an object signature in hypersensor data of claim 1, wherein the anomaly suppression module is configured to apply suppression factors to pixel spectrum determined to be an anomaly.

6. The system for anomaly resistant detection and identification of an object signature in hypersensor data of claim 1, further comprising:
    a data preparation module configured to partition the hypersensor data and to provide chunks of the hypersensor data to the mask and filter module.

7. The system for anomaly resistant detection and identification of an object signature in hypersensor data of claim 6, wherein the data preparation module is configured to apply background information learned in one or more previous chunks to a current chunk.

8. A system for anomaly resistant detection and identification of an object signature in hypersensor data, comprising:
    a chemical hypersensor which senses multiple different attributes of a chemical gas or vapor at each of multiple different observation times sensed by the chemical hypersensor and generates hypersensor data; and
    a mask and filter module configured to receive and process the hypersensor data using a multi-dimensional matched filter to distinguish spectra uncommon in the scene and not orthogonal to the target that produce anomaly-generated false alarms from target spectrum and suppress the spectra uncommon in the scene and not orthogonal to the target that produce anomaly-generated false alarms;
    wherein the multi-dimensional matched filter includes a set of orthogonally matched filters for one or more targets, the matched filters being trained on common background only;

wherein the orthogonally matched filters provide a multi-dimensional filter matrix that includes rows which form a set of mutually orthogonal filter vectors.

9. The system for anomaly resistant detection and identification of an object signature in hypersensor data of claim 8, wherein the hypersensor data represents a hyperspectral cube.

10. The system for anomaly resistant detection and identification of an object signature in hypersensor data of claim 8, wherein each member of the set of orthogonally matched filters results in a unity value dot product with its target.

11. The system for anomaly resistant detection and identification of an object signature in hypersensor data of claim 8, wherein processing hypersensor data includes applying the multi-dimensional matched filter to pixel spectra to produce a vector of filter products for each spectrum.

12. The system for anomaly resistant detection and identification of an object signature in hypersensor data of claim 11, wherein the spectra that produce anomaly-generated false alarms are distinguished by evaluating differences in elements of the vectors.

* * * * *